United States Patent
Heide et al.

(10) Patent No.: US 9,310,232 B2
(45) Date of Patent: Apr. 12, 2016

(54) METHOD FOR CALIBRATING A SENSOR WITHIN AN ENCLOSURE; SENSOR, DISPOSABLE, AND TREATMENT DEVICE INCLUDING A LIKE SENSOR

(75) Inventors: Alexander Heide, Eppstein (DE); Klaus Metzner, Friedrichsdorf (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 536 days.

(21) Appl. No.: 12/918,837

(22) PCT Filed: Feb. 24, 2009

(86) PCT No.: PCT/EP2009/001306
§ 371 (c)(1),
(2), (4) Date: Oct. 21, 2010

(87) PCT Pub. No.: WO2009/106293
PCT Pub. Date: Sep. 3, 2009

(65) Prior Publication Data
US 2011/0048101 A1 Mar. 3, 2011

(30) Foreign Application Priority Data
Feb. 25, 2008 (DE) .................... 10 2008 010 948

(51) Int. Cl.
*G01L 27/00* (2006.01)
*G01D 18/00* (2006.01)
*A61M 1/36* (2006.01)

(52) U.S. Cl.
CPC ............ *G01D 18/008* (2013.01); *A61M 1/367* (2013.01); *A61M 2205/3569* (2013.01); *A61M 2205/3592* (2013.01); *A61M 2205/70* (2013.01); *A61M 2209/02* (2013.01)

(58) Field of Classification Search
USPC ............................................ 73/1.57
See application file for complete search history.

(56) References Cited

U.S. PATENT DOCUMENTS

| 5,659,125 A | 8/1997 | Ernst |
| 6,468,241 B1 | 10/2002 | Gelfand et al. |
| 6,695,806 B2 * | 2/2004 | Gelfand et al. .............. 604/6.09 |
| 6,841,401 B1 * | 1/2005 | Nishimoto et al. ............. 438/10 |
| 6,850,859 B1 | 2/2005 | Schuh |
| 7,146,861 B1 | 12/2006 | Cook et al. |
| 7,219,021 B2 | 5/2007 | Liu et al. |
| 8,641,965 B2 * | 2/2014 | Martel ...................... A61L 2/07 206/569 |
| 2003/0088203 A1 | 5/2003 | Gelfand et al. |
| 2005/0148819 A1* | 7/2005 | Noguchi et al. .............. 600/133 |
| 2007/0126794 A1 | 6/2007 | Schick et al. |
| 2007/0240578 A1* | 10/2007 | DiLeo ............................. 96/417 |

FOREIGN PATENT DOCUMENTS

DE 602 12 805 T2 12/2006
JP S63 154956 A 6/1988
(Continued)

OTHER PUBLICATIONS

International Search Report, PCT/EP2009/001306, mailed Oct. 27, 2009.

*Primary Examiner* — Hezron E Williams
*Assistant Examiner* — Mark A Shabman
(74) *Attorney, Agent, or Firm* — Kenyon & Kenyon LLP

(57) ABSTRACT

The invention relates to a method for calibrating sensors, in particular RFID sensors, within an enclosure such as, e.g., a sterilization chamber. It furthermore relates to a sensor calibrated by the method of the invention, a disposable device including such a sensor, as well as a treatment device.

25 Claims, 3 Drawing Sheets

(56) References Cited

FOREIGN PATENT DOCUMENTS

| | | |
|---|---|---|
| JP | 2007-509712 A | 4/2007 |
| WO | 93/21964 | 11/1993 |
| WO | 2002/022187 A2 | 3/2002 |
| WO | 2005/042065 A2 | 5/2005 |
| WO | 2005/077262 A1 | 8/2005 |
| WO | 2007/102842 A2 | 9/2007 |

* cited by examiner

METHOD FOR CALIBRATING A SENSOR WITHIN AN ENCLOSURE; SENSOR, DISPOSABLE, AND TREATMENT DEVICE INCLUDING A LIKE SENSOR

CROSS REFERENCE TO RELATED APPLICATIONS

This is a 371 national phase application of PCT/EP2009/001306 filed Feb. 24, 2009, claiming priority to German Patent Application No. 10 2008 010948.7 filed Feb. 25, 2008.

FIELD OF INVENTION

The present invention relates to a method for calibrating a sensor. It furthermore relates to a sensor, a disposable device, and a treatment device.

In a number of methods that are known from practice, the value of one or several parameters is repeatedly measured in order to check and control the method. Such methods are known both from the industrial and medical fields. Thus in the field of medicine, e.g. in the dialysis treatment of a patient employing an extracorporeal blood circulation, the venous and arterial pressures in the extracorporeal blood circulation are measured, and the method is controlled in accordance with the measured values.

BACKGROUND OF THE INVENTION

In order to determine the pressure in the extracorporeal blood circulation, the latter may be provided with "tap lines" (pressure derivations) in order to pass the pressure in the extracorporeal circulation on to a pressure sensor by means of a gas column. These tap lines represent "open" locations of the extracorporeal circulation and must be protected for reasons of hygiene, i. a. by sterile filters ("transducer protector"). A failure of these filters or protective means in general can expose the patient to the risk of a cross-contamination.

Another known method for measuring the extracorporeal pressure is implemented with the aid of so-called "pressure domes". Here the tubing system remains closed, with the pressure values being transmitted from the blood to the machine via an impermeable membrane. To this end, a reusable pressure sensor is disposed in the extracorporeal circulation. The sensor has to satisfy considerable demands to hygiene, drift of measurement values, etc., over a comparatively long period of time such as two years to ten years.

Accordingly, pressure sensors for one-way articles or disposables which transmit measured values by wire or also wirelessly are also known in the prior art. In the example of the extracorporeal blood circulation, they are situated inside the one-way tubing system and are discarded together with the disposable following the treatment. Such pressure sensors for disposable devices do, however, require a calibration that must be performed individually for each sensor, whereby their manufacture is rendered costly. The supplier of the sensors moreover has to supply calibration data in separate data memories together with the sensors, as is described, e.g., in U.S. Pat. No. 6,695,806 B2 to CHF Solutions. It is in particular the high costs caused by the connections necessary for calibration of each individual sensor which is prohibitive for a use of these sensors in the large and very large piece numbers in which most one-way articles are manufactured and used.

SUMMARY OF THE INVENTION

It is the object of the present invention to propose another method for calibrating a sensor. Moreover it is intended to specify a sensor calibrated by means of the method of the invention, a disposable (a one-way or disposable article) including such a sensor, and a treatment device including such a sensor and/or such a disposable.

Thus, in accordance with the invention, a method for calibrating at least one sensor, in particular a RFID (Radio Frequency Identification) sensor is being proposed, wherein the sensor comprises at least one memory means for storing at least one value of at least one parameter. The parameter may be of a physical, chemical or biological nature such as pressure, temperature, conductivity, concentration etc., or of any other nature.

The sensor may comprise an interface for a RFID component with r/w (read/write) memory, which allows calibration of the sensor as early on as during its manufacturing process; it may moreover store information such as product identification data for a later examination of a means connected to the sensor, in particular a medical means such as a disposable or a reusable object, as to their aptness for the selected treatment method. In the framework of the invention, a memory also designates a plurality of memories which may be located separate from each other.

The method includes the step of placing the sensor inside an enclosure, with a known value of the parameter prevailing inside the enclosure at least at one point of time at which the sensor is disposed inside the enclosure.

The sensor is preferably suited for storing one or several values of one or several parameters that prevail inside the enclosure during its presence.

In accordance with the invention, an "enclosure" is understood to be a confined space. Similarly, in accordance with the invention an "enclosure" is also understood to be any semi-open or open location in which the parameter to which the sensor is to be calibrated is present—at least at one point of time at which the sensor is disposed at this location—with a value which is known with sufficient accuracy for the purposes of calibrating the sensor.

In accordance with the invention, the "value" of the parameter is understood to be a variable manifestation of the parameter itself. Thus, e.g., the FIG. 3 in the indication "3 bar" is to be understood as a value within the meaning of the invention, whereas the dimension "bar" indicates the parameter itself—in this instance the pressure. Mention herein below of a parameter may furthermore always extend to a plurality of parameters whenever it is discernible to the skilled person that these explanations concerning the parameter also apply.

In the performance of the calibration method of the invention, the value of the parameter prevailing inside the enclosure is determined at one or several points of time by the sensor disposed in the enclosure. This may be done, e.g., with the aid of a measurement process or by some other determination method or combinations thereof. At the at least one point of time at which the parameter value prevailing inside the enclosure is to be measured by the sensor, a signal to determine and store the parameter value, which is suited to be received by the sensor inside the enclosure, may be transmitted to the sensor. This signal which is sent to the sensor may at the same time contain information concerning the known parameter value actually prevailing inside the enclosure. The parameter value measured or determined by the sensor may be used immediately or also at a later time for generating a calibration curve. The calibration curve may be stored in the sensor.

One advantage which is obtainable through the method of the invention for calibrating a sensor resides in the fact that by placing the sensor inside an enclosure—in the sense of any kind of introduction into the enclosure—under conditions of the enclosure inner space that are known at least at one point of time, a time-consuming, apparative connection of the sensor to its calibration may advantageously be omitted. Rather, for instance, a passage of the sensor through the enclosure which will in any case take place, for instance during its manufacture, may advantageously be "shared" for a calibration. The method of the invention is therefore characterized by a calibration of the sensor involving comparatively low complexity and costs.

In contrast with the known use of open tap lines or pressure domes, further advantages consist in the fact that machine-side pressure sensors are not necessary any more, and in that no costs for maintenance or the like are incurred any more. Neither does the utilization of sensors manufactured in accordance with the invention necessitate the use of "transducer protectors" any more, particularly in the medical field, with a risk of cross-contaminations by way of the pressure derivations nevertheless not existing any more: The use of sensors manufactured in accordance with the invention allows to measure the parameter inside an air-free, closed system. In the medical field, a measurement may advantageously take place without contact between blood and environment or air, respectively, at a minimum contact surface between sensor and blood.

Thus it is proposed in a particularly preferred embodiment to perform the method with the aid of a sterilization chamber in which the sensor is placed. In such sterilization chambers, sterilization is usually performed by using, i. a., steam, EtO, e-beam, plasma, radiation, etc.

Sterilization chambers are as a general rule characterized by the fact that—particularly in industrial sterilization—processes unfold under controlled and accurately known process conditions. While performing the method of the invention involving a sterilization chamber, it is therefore advantageously possible to make use of a sterilization process which will in any case be carried out inside a sterilization chamber, in order to calibrate the sensor without any of the significant additional complexity described in the foregoing. It is not necessary to separately create suitable environmental conditions for a calibration of the sensor.

The method of this embodiment in accordance with the invention is particularly well suited for calibrating sensors which have to be sterile for their utilization. The sterilization process which will in any case take place may at the same time be "shared" for a calibration of the sensor.

An again further preferred embodiment of the method of the invention provides that a time period is also stored in the memory means of the sensor in addition to the above-discussed at least one parameter value. With corresponding signalling, this time period may indicate, e.g., for how long the sensor was exposed to particular conditions. Reading the information stored in the memory means of the sensor may thus result, thanks to the time information, in additional statements which may advantageously be used for information concerning processes taking place inside the enclosure.

In the example of the sterilization chamber as an enclosure within the meaning of the method of the invention, the stored time period in combination with a corresponding control of the sensor may i. a. allow a statement as to whether the sensor—and, for instance, an element connected thereto such as the disposable described further below—has been exposed to a sterilization process for a sufficiently long time. If the sterilization should take place at approx. 120° C. and at the associated pressure in the case of steam sterilization, for instance, and if the sensor must be exposed to this temperature for a minimum time period in order to attain positively ensured sterility, for instance, then it is possible to check at a later point of time whether the sensor—and optionally a disposable connected to it—may be rated sterile or not, by using the stored time period or stored data permitting a conclusion as to the time period. Where a sensor was not kept at the prescribed temperature for a sufficiently long time, this sensor and an element connected to it, such as a disposable, may be identified as not being sterile and thus discarded based on the stored time information. In this way, every sensor calibrated in accordance with the method of this embodiment in accordance with the invention—and elements connected to it—receive an individual sterility certificate.

The method of the invention in the present embodiment furthermore allows an additional check of the conditions which actually prevailed inside the enclosure during the sensor's presence there.

It will be evident to the skilled person that these explanations, which were made for the example of the sterilization chamber, may also be transposed to enclosures other than the sterilization chamber. Such enclosures may be pressure chambers and the like. This also includes enclosures wherein it is not intended to create sterile conditions but merely to reduce the germ count (low degree of bacterial contamination).

In accordance with an again further preferred embodiment of the method of the invention, a plurality or multiplicity of sensors, in particular a batch or a set of sensors, is jointly placed inside the enclosure so as to be simultaneously located there at least at one point of time. In this way, the plurality of sensors is calibrated at a same time and again—in accordance with the above description—without any additional apparative complexity. Signals directed to the sensors from outside the enclosure may be received by any one sensor from among the plurality of sensors and may result in a corresponding reaction by all of the sensors. In accordance with the invention it is therefore advantageously possible to communicate with a plurality or multiplicity of sensors without physical contact, such as by way of a line connection, whereby the complexity of calibrating as a whole is kept extremely low.

If a placement position in the enclosure is known for each one of the sensors, which may in particular be true when the enclosure is charged automatically, then the respective information concerning the conditions inside the enclosure that are stored in the respective single memory means of the sensors may enable or support a check of the processes taking place inside the enclosure, such as, e.g., a sterilization process. If in addition the placement position of the sensor in the enclosure is known, it is moreover possible to determine from the placement position an accurate pressure and/or temperature profile (as well as any other profiles) for the enclosure, which may represent an important and cost-efficient contribution to complex in-process checks and validations.

In an again further preferred embodiment, the sensor is connected to a reusable article or to a disposable or single-use article—i.e., it is associated to the latter in an arbitrary manner, irrespective of whether or not a positive and/or frictional connection between sensor and disposable exists—and is present inside the enclosure jointly with the latter. The treatment undergone by the sensor inside the enclosure is thus at the same time undergone by the disposable, and vice versa. This is of particular interest, e.g., in the sterilization of the disposables inside a sterilization chamber, for in this way sterilization is performed not only on the disposable, but at the same time on the sensor which may possibly get into contact with bodily fluids at a later point of time.

Moreover, the sensor in this embodiment of the method of the invention is preferably exposed to the same enclosure conditions as the reusable article or the disposable. The sensor may then preferably store values of parameters to which the reusable article or the disposable is also exposed.

This method moreover possesses the advantages described further above—to which reference is explicitly made here in order to avoid repetitions—namely, a simple, calibration of the sensor of a disposable involving low apparative complexity and low costs, during a sterilization step inside a sterilization chamber which is in any case mandatory for the disposable.

It is noted that these advantages are not restricted to the sterilization process inside a sterilization chamber. They are rather also obtainable when jointly placing the sensor and the disposable in any enclosures other than a sterilization chamber.

In an again further preferred embodiment, the present invention relates to a method for calibrating at least one sensor, in particular an RFID sensor comprising a memory means for storing at least one value of at least one, in particular physical or chemical or biological, parameter, including disposing the sensor inside an enclosure in which a known value of the parameter prevails at least at one point of time, wherein the sensor is disposed inside the enclosure while being connected to a means, in particular a medical means—a disposable or a reusable object; and a known value of the parameter prevailing in the enclosure is stored with the aid of the memory means. The method of the invention in accordance with this embodiment may preferably be combined with arbitrary method features which are presently also being disclosed, to the extent that the person having skill in the art can perceive a combining capability. Such combinations are herewith expressly encompassed by the invention.

The object of the invention is also achieved through a sensor, through a disposable, and through a treatment device, in particular a dialysis apparatus such as, e.g., a hemodialysis apparatus. As all of the advantages discussed in the foregoing in connection with the method of the invention may also be achieved undiminished with the sensor of the invention, the disposable, and the treatment device, express reference is made to the above discussion of the advantages obtainable among others, so as to avoid repetitions. The disposable may be any one-way article, in particular medical disposables, above all dialysis disposables such as extracorporeal blood tube sets and the like. An additional advantage afforded by a disposable in accordance with the invention is the fact that the service life of its sensor as a general rule need not exceed a few hours up to a few days due to the one-time-use of the disposable. Manufacture of the sensors may be correspondingly simple and cost-efficient.

BRIEF DESCRIPTION OF THE DRAWINGS

The present invention shall in the following be explained in more detail by way of the annexed drawings, wherein.

DETAILED DESCRIPTION OF THE DRAWINGS

Figure 1:
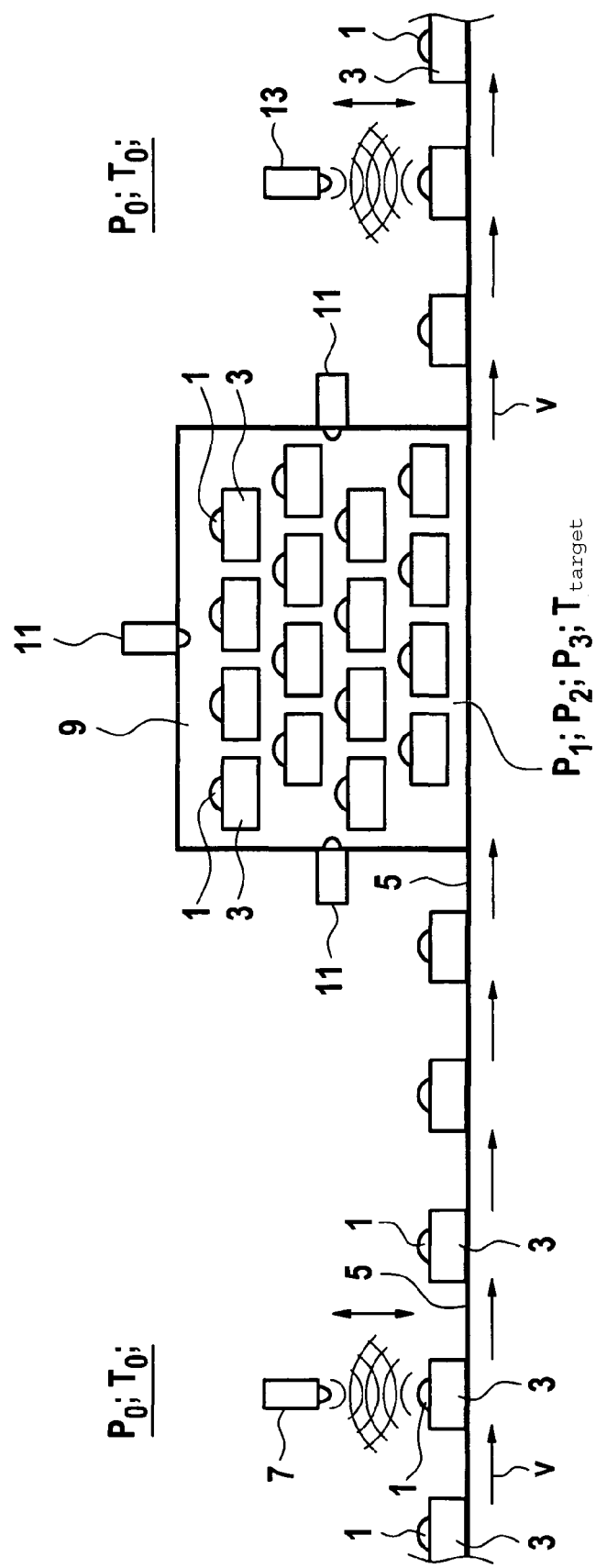
FIG. 1 shows the flow of an exemplary embodiment of the method of the invention.

FIG. 1 shows a possible flow of the method of the invention by the example of schematically simplified steam-sterilized blood tube sets representing one example of disposables 3, with each blood tube set 3 including at least one RFID sensor 1. The steps of the method of the invention as represented in the exemplary embodiment illustrated in FIG. 1 are subsequent to a known production method for the tube sets 3. In the process, the disposables 3 equipped with the RFID sensors 1 are separately present on a conveyor belt 5. The direction of movement of the conveyor belt 5 is indicated by arrows v in FIG. 1. The sensors 1 are queried in a first functional test at the left margin of FIG. 1 by means of a RFID reader unit 7. Hereby it may be ascertained whether or not the disposable 3 is equipped with a sensor 1 and whether this sensor 1 correctly transmits its identification when contacted by radio.

By virtue of a plausibility test it is furthermore possible to check whether the sensor 1 correctly indicates the normal ambient temperatures $T_0$ and $P_0$, prevailing during the method step of the left margin of FIG. 1, within a predetermined range of tolerance. In case a disposable 3 or its sensor 1, respectively, should not pass this first plausibility test and/or functional test, the corresponding disposable 3 together with its sensor 1 may be discarded as rejects. The memories of the sensors 1 of those disposables 3 identified as not being rejects may be written and serialized with production data which may relate both to the sensor 1 and the disposable 3, as well as with calibration data. By storing production data the individual product may later on easily be tracked according to need.

The disposables 3 not evaluated as rejects are transported further on the conveyor belt 5 into an enclosure 9 to be charged with disposables 3. In the example of FIG. 1, the enclosure 9 is configured as a sterilization chamber in which a sterilization process takes place. Where the enclosure is charged in an automated manner, the placement position of each disposable 3 inside the enclosure 9 may be accounted for in a simple manner. In the sterilization process of FIG. 1, pressure and temperature are raised (the latter up to approx. 120° C.) inside the enclosure 9, as is explained in FIG. 3 that will be discussed below. At arbitrary points of time a signal—preferentially identical for all of the sensors 1—is output from one or several RFID transmission antennae 11. The signal causes the respective current pressure values and optionally the temperature values measured by the respective sensor 1 to be stored. The corresponding reference pressure values, i.e., the pressure values and optionally the temperature values which actually prevailed inside the enclosure 9 at that respective point of time may also immediately be transferred to the sensor memory by means of a signal. This may, however, also take place at a later point of time, even after the sensors 1 have left the enclosure 9. Emission of such a signal to the sensors 1 present inside the enclosure 9 by means of the RFID transmission antennae 11 may be repeated for an arbitrary number of times. In order to plot a linear calibration curve, even only a single time of measurement during the stay inside the enclosure is sufficient if a second time of measurement is provided before or after the stay inside the enclosure (determination of the zero value). This may, for example, be the maximum pressure in a stationary phase of the sterilization process inside the enclosure 9. The method of the invention may accordingly also be performed without emission of a signal by the RFID transmission antennae 11.

After leaving the enclosure 9 upon completion of the sterilization process and having been redeposited on the conveyor belt 5, the disposables 3 again singly pass through a RFID reader unit 13. Here, in turn, a plausibility test is carried out which may include an examination whether the RFID sensor 1 of each disposable 3 reports correctly. Moreover it may again be examined whether the displayed temperature and/or pressure value measured by the sensor 1 after leaving the enclosure 9 conforms with the actual environmental conditions $T_0$ and $P_0$. Additional functional and/or plausibility examinations are equally possible.

Disposables 3 having sensors 1 which did not pass one of these tests are again treated as rejects. For the remaining disposables 3 recognized as not being rejects, one or several calibration curve(s) is/are calculated based on the (calibration) values stored in the memory unit(s) of their sensors 1 and stored in the memory of the sensor 1, as may be seen in FIG. 2. In this production step it is moreover possible to write data relating to sterilization and expiration dates and the like into the memories of the sensors 1. If the placement positions of the individual sensors 1 inside the enclosure 9 are known, the sterilization process inside the enclosure 9 may be checked by generating an accurate profile of temperatures inside the enclosure 9.

Figure 2:
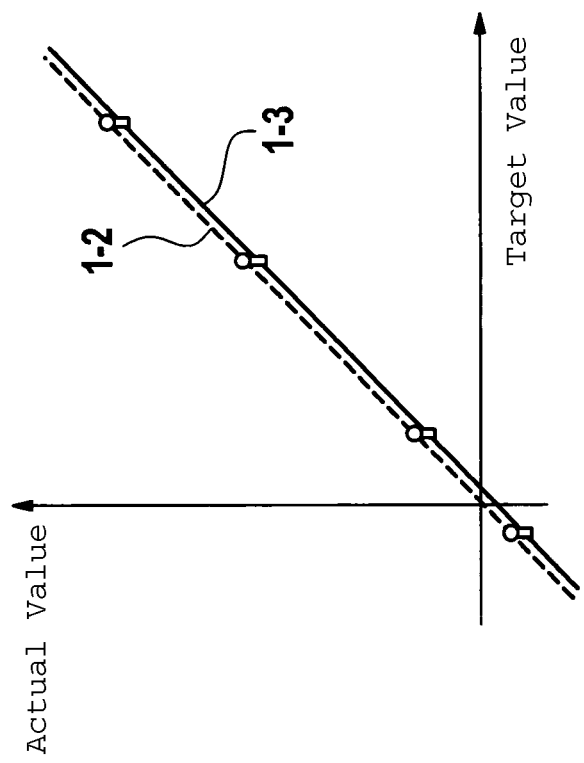
FIG. 2 shows the manner of proceeding for a plausibility test and a gradient adaptation in the framework of an exemplary embodiment of the method of the invention.
Figure 2:
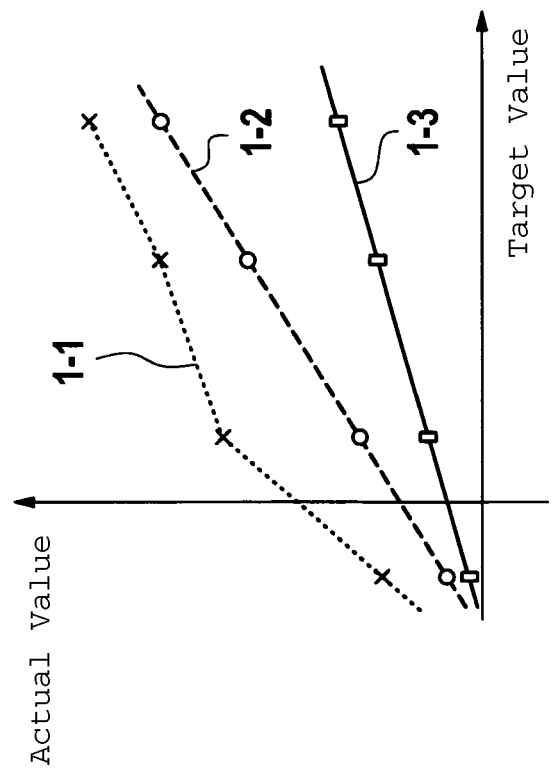

FIG. 2 shows in its left-hand representation the pressure values measured by three sensors 1-1, 1-2 and 1-3, whereby one respective calibration curve each may be calculated and stored in the memory of the respective sensor. As may be seen in the left-hand representation of FIG. 2, the measured pressure values of sensor 1-1 are not situated on a straight line, for which reason this sensor 1-1 is discarded as reject together with the associated disposable. For sensors 1-2 and 1-3 which were recognized to not be rejects, corrected gradient evolutions are established for their calibration, as may be seen in the right-hand representation of FIG. 2. The evolutions are stored.

Figure 3:
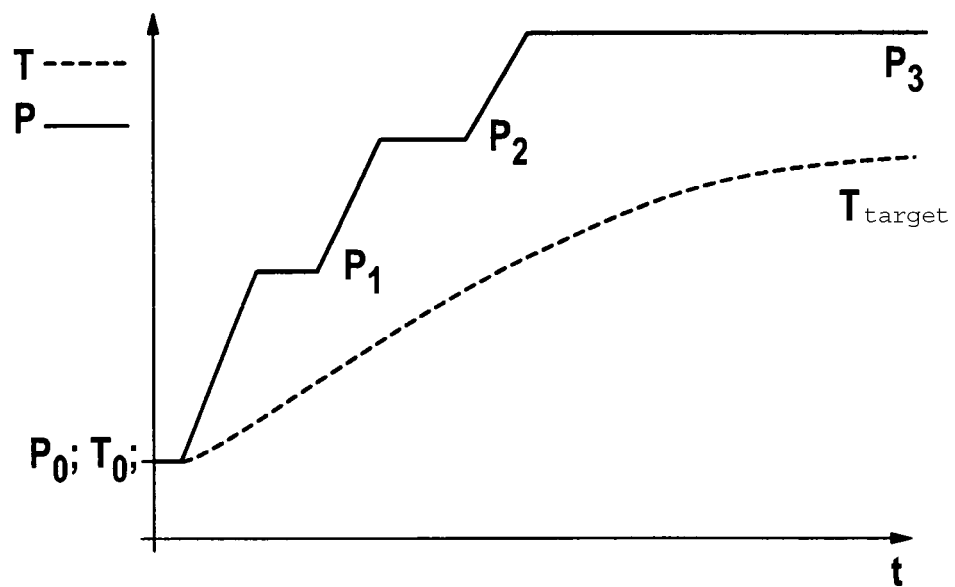
FIG. 3 shows the changes of pressure and temperature inside an enclosure over the course of time.

FIG. 3 shows the stepwise pressure increase from $P_0$ to $P_1$, from $P_1$ to $P_2$, and from $P_2$ to $P_3$ versus the time t, which was already discussed in connection with FIG. 1. Here the internal temperature of the enclosure 9 gradually rises from the ambient pressure $T_0$ to the target value $T_{target}$. As the pressure accurately corresponds to the temperature in the case of a steam sterilization at operating parameters on the saturated steam curve of water vapor, the temperature value may be utilized for a process evaluation. This means that a sensor of a disposable which had not be exposed to the prescribed minimum temperature for a sufficient time period may be identified as not being sterile and sorted out. In this way, each disposable may individually receive a sterility certificate in a simple manner. In the present example this is also possible without a temperature measurement while only performing pressure measurements, as will be evident to the person having skill in the art.

The invention claimed is:

1. A method for calibrating at least one sensor, said at least one sensor comprising a memory means for storing at least one value of at least one calibration parameter, the method comprising:
    placing the at least one sensor inside an enclosure wherein a known value of said at least one calibration parameter prevails at least at one point of time; and
    storing at least one value of at least one calibration parameter prevailing inside the enclosure in the memory means at least at one point of time during a sterilization process;
    wherein the enclosure is a sterilization chamber.
2. The method according to claim 1, wherein the at least one calibration parameter is a pressure, a temperature, a concentration, or a conductivity.
3. The method according to claim 2, further comprising: storing a time period in the memory means.
4. The method according to claim 3, further comprising: determining a completion of the sterilization process based on the stored time period.
5. The method according to claim 1, further comprising: storing a time period in the memory means.
6. The method according to claim 3, further comprising: determining a completion of the sterilization process based on the stored time period.
7. The method according to claim 1, wherein a plurality of sensors is jointly placed in the enclosure.
8. The method according to claim 1, wherein the at least one sensor is placed inside the enclosure while being coupled to a disposable device.
9. A sensor calibrated by the method according to claim 1.
10. A disposable device comprising at least one sensor according to claim 9.
11. A treatment device comprising at least one disposable device according to claim 10.
12. A dialysis apparatus comprising at least one disposable device according to claim 10.
13. A treatment device comprising at least one sensor according to claim 9.
14. The treatment device according to claim 13 further comprising at least one disposable device.
15. A dialysis apparatus comprising at least one sensor according to claim 9.
16. The dialysis apparatus according to claim 15 further comprising at least one disposable device.
17. The dialysis apparatus according to claim 16, wherein the at least one calibration parameter is a pressure, a temperature, a concentration, or a conductivity.
18. The method according to claim 1, wherein the at least one sensor is a RFID sensor.
19. The method according to claim 1, wherein the at least one calibration parameter is a physical, chemical, or biological parameter.
20. The method according to claim 1, wherein a batch of sensors is jointly placed in the enclosure.
21. The method according to claim 1, further comprising: coupling the at least one sensor to a disposable device before placing the at least one sensor inside the enclosure.
22. The method according to claim 1, further comprising: conveying the at least one sensor on a conveyor belt before placing the at least one sensor inside the enclosure.
23. The method according to claim 1, further comprising: performing at least one of:
    a functional test to confirm whether the at least one sensor correctly transmits its identification when contacted by a radio; or
    a plausibility test to confirm whether the at least one sensor correctly indicates an ambient temperature and an ambient pressure prevailing at one point of time before placing the at least one sensor inside the enclosure.
24. The method according to claim 23, wherein if the at least one sensor fails the at least one functional test or plausibility test, the at least one sensor is discarded.
25. The method according to claim 23, wherein if the at least one sensor passes the at least one functional test or plausibility test, the at least one sensor is transported further on the conveyor belt into the enclosure.

* * * * *